(12) United States Patent
Lee et al.

(10) Patent No.: US 8,987,345 B2
(45) Date of Patent: Mar. 24, 2015

(54) DENTAL BONDING AGENT AND COATING AGENT

(71) Applicant: National Taiwan University, Taipei (TW)

(72) Inventors: Bor-Shiunn Lee, Taipei (TW); Da-Ming Wang, Taipei (TW)

(73) Assignee: National Taiwan University (TW)

( * ) Notice: Subject to any disclaimer, the term of this patent is extended or adjusted under 35 U.S.C. 154(b) by 0 days.

(21) Appl. No.: 13/790,359

(22) Filed: Mar. 8, 2013

(65) Prior Publication Data

US 2014/0148526 A1 May 29, 2014

(30) Foreign Application Priority Data

Nov. 26, 2012 (TW) .............................. 101144184 A

(51) Int. Cl.
*A61K 6/00* (2006.01)
*A61K 6/083* (2006.01)
*C08L 33/00* (2006.01)
*C09D 133/00* (2006.01)

(52) U.S. Cl.
CPC ............... *A61K 6/0023* (2013.01); *C08L 33/00* (2013.01); *C09D 133/00* (2013.01)
USPC ....................................................... 523/118

(58) Field of Classification Search
None
See application file for complete search history.

(56) References Cited

U.S. PATENT DOCUMENTS

| | | | |
|---|---|---|---|
| 4,381,386 A * | 4/1983 | Ritter et al. ................... 526/239 |
| 5,919,836 A * | 7/1999 | Reinhardt ..................... 523/118 |
| 6,384,104 B1 * | 5/2002 | Chang et al. .................. 523/105 |
| 6,512,068 B1 * | 1/2003 | Nakatsuka ..................... 526/277 |
| 6,994,551 B2 * | 2/2006 | Wang et al. .................... 433/226 |
| 7,090,721 B2 * | 8/2006 | Craig et al. ..................... 106/35 |
| 7,156,911 B2 * | 1/2007 | Kangas et al. .................. 106/35 |
| 7,312,259 B2 * | 12/2007 | Adamo et al. .................. 523/342 |
| 7,361,216 B2 * | 4/2008 | Kangas et al. .................. 106/35 |
| 7,442,734 B2 * | 10/2008 | Mori et al. ..................... 524/107 |
| 7,449,499 B2 * | 11/2008 | Craig et al. .................... 523/118 |
| 7,452,924 B2 * | 11/2008 | Aasen et al. ................... 523/116 |
| 7,601,767 B2 | 10/2009 | Ruppert et al. |
| 7,649,029 B2 * | 1/2010 | Kolb et al. ..................... 523/117 |
| 8,022,114 B2 * | 9/2011 | Sang et al. ..................... 523/118 |
| 8,029,286 B2 * | 10/2011 | Craig et al. ................ 433/228.1 |
| 8,071,662 B2 * | 12/2011 | Craig et al. .................... 523/116 |
| 8,198,343 B2 * | 6/2012 | Liu ................................ 522/24 |
| 8,278,368 B2 * | 10/2012 | Rusin et al. .................... 523/116 |
| 8,440,741 B2 * | 5/2013 | Sang et al. ..................... 523/116 |
| 2004/0229973 A1 * | 11/2004 | Sang et al. ..................... 523/118 |
| 2005/0176844 A1 * | 8/2005 | Aasen et al. ................... 523/118 |
| 2005/0252413 A1 * | 11/2005 | Kangas et al. .................. 106/35 |
| 2006/0205838 A1 * | 9/2006 | Velamakanni et al. ....... 523/115 |
| 2007/0142498 A1 * | 6/2007 | Brennan et al. ............... 523/118 |
| 2009/0258966 A1 * | 10/2009 | Hirayama et al. ............. 523/118 |
| 2009/0305194 A1 * | 12/2009 | Rusin et al. ................. 433/217.1 |
| 2011/0165539 A1 * | 7/2011 | Sang et al. .................. 433/217.1 |

FOREIGN PATENT DOCUMENTS

| | | |
|---|---|---|
| TW | 200534868 | 11/2004 |
| TW | I262795 | 10/2006 |

* cited by examiner

*Primary Examiner* — James J Seidleck
*Assistant Examiner* — Peter A Salamon
(74) *Attorney, Agent, or Firm* — YANGIPCo, PLLC

(57) ABSTRACT

The present disclosure provides a dental bonding agent which may comprise a composite resin containing an ingredient selected from acrylic resins, a primer comprising an amphiphile, and at least one phosphate ester, and a solvent. The dental bonding agent may be applied for resin restoration, prosthetic adhesion, enhancing adhesive strength between dentin and artificial post, and tooth coating. The present disclosure also provides a coating agent which may comprise a dental bonding agent as defined above, a pigment, and an inorganic filler.

4 Claims, 10 Drawing Sheets
(5 of 10 Drawing Sheet(s) Filed in Color)

DENTAL BONDING AGENT AND COATING AGENT

CROSS-REFERENCE TO RELATED APPLICATION(S)

This application claims priority to Taiwan Patent Application No. 101144184, filed on Nov. 26, 2012, the disclosure of which is hereby incorporated by reference in its entirety.

FIELD OF THE DISCLOSURE

The present disclosure relates to a dental bonding agent and a coating agent. More particularly, the present disclosure relates to a bonding agent for endodontic therapy and a coating agent for application to enamel surface.

DESCRIPTION OF THE RELATED ART

The dental pulp tissue in the root canal may come into contact with the outside environment as a result of dental caries. The pulp usually may suffer from acute/chronic pulpitis or necrosis. Endodontic therapy may be an essential treatment to maintain dental health and avoid tooth extraction, which includes removing the necrotic pulp tissue, completely cleaning the root canal, enlarging and filling the root canal to avoid repeated infection, and restoring the conformation of tooth to maintain its normal function. Root canal-treated teeth with insufficient coronal structure generally require radicular post, including post and core, for crown restoration. The post provides support for the tooth when confronting strong occlusion pressure.

In clinical dental restoration, the composite resin is generally used for direct restoration. However, the hydrophobic resin material has poor adhesion to hydrophilic dentin. Another problem is that the volume of conventional composite resin shrinks after polymerization, causing structural deformation of the adhesive interface and microleakage. To solve the above problems, specific adhesive systems are applied clinically to assist the adhesion between the resin material and the tooth. Said adhesive system comprises a dental resin cement, which is located between the post and dentin.

However, dentin has complex components. Dentin is less mineralized tissue with hydrophilic collagen fibers as well as numerous dentinal tubules from pulp to dentin surface, so that dentin is a highly water-containing and water-permeable tissue. Therefore, the conventional adhesive system provides poor assistance for adhesion on dentin surface.

The smear layer also affects the adhesion. The smear layer is a mixture formed on tooth surface containing denatured organic components (e.g. collagen) induced by heat from treatment of cutting, powders of treated tooth, dentin fluid, saliva, microbes, and the like. The smear layer seriously and adversely affects the adhesion between the restoration materials and dentin, and thereby reduces their fitting. A conventional solution is to remove the smear layer by EDTA or to make the smear layer part of the adhesive layer by using dentin bonding agent. Recent developments of self-etching adhesive systems enhances adhesion by incorporating the smear layer into adhesive layer.

Though various adhesive systems have been developed and commercialized, there is still a need for an adhesive system that can improve adhesion and solve the above problems.

Tooth whitening treatment is performed by applying hydrogen peroxide or carbamide peroxide. The treatment usually takes one week or longer. Another option for tooth whitening is to use a coating agent. However, conventional coating agents cannot satisfy all of the following requirements: harmless to the human body, effective shading of undesired color, natural color, and toothbrush-removable. Accordingly, there is still a need for a coating agent that can satisfy the above requirements.

SUMMARY OF THE DISCLOSURE

The present disclosure provides a dental bonding agent which may comprise a composite resin containing an ingredient selected from acrylic resins, a primer comprising an amphiphile and at least one phosphate ester, and a solvent.

The present disclosure also provides a coating agent comprising a dental bonding agent as defined above, a pigment, and an inorganic filler.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE EMBODIMENTS

Figure 1:
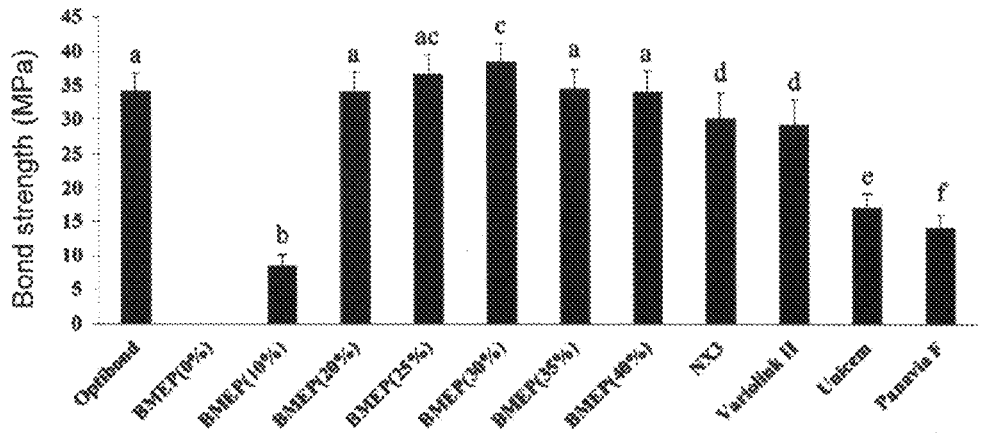
FIG. 1 illustrates microtensile bond test results.

The present disclosure provides a dental bonding agent which may comprise a composite resin, a primer comprising an amphiphile and at least one phosphate ester, and a solvent.

The composite resin may comprise at least one acrylic resin. The acrylic resins can be selected from, for example, bisphenol A glycerolate dimethacrylate (Bis-GMA), triethylene glycol dimethacrylate (TEGDMA), methyl acrylate (MMA), dipentaerythritol penta acrylate monophosphate (PENTA), 10-methacryloyloxydecamethylene malonic acid (MAC-10), 10-methacryloyloxy decamethylene phosphoric acid (10-MDP), biphenyl dimethacrylate (BPDM), 4-methacryloyloxyethyl trimellitate anhydride (4-META), 4-methacryloyloxyethyl trimellitic acid (4-MET), N-methacryloyl-5-aminosalicylic acid (5-NMSA), 4-acryloyloxyethyl trimellitate anhydride (4-AETA), mono-2-methacryloyloxyethyl phthalate (MMEP), 2-methacryloyloxyethyl phenyl phosphoric acid (Phenyl-P), an addition product of pyromellitic dianhydride and 2-hydroxyethyl methacrylate (PMDM), urethane dimethacrylate (UDMA), 2-hydroxyethyl methacrylate-phosphate (HEMA-phosphate), 2-hydroxyethyl methacrylate (HEMA), N-phenylglycine glycidyl methacrylate (NPG-GMA), and N-(p-tolyl)glycine glycidyl methacrylate (NTG-GMA), which can be used alone or in combination. In one embodiment, the acrylic resins is preferably selected from Bis-GMA, TEGDMA, or a combination thereof.

The primer is an adhesion promoter, which may comprise an amphiphile and at least one phosphate ester. In a preferred embodiment, the phosphate ester is bis[2-(methacryloyloxy)-ethyl]phosphate (BMEP) having the following formula:

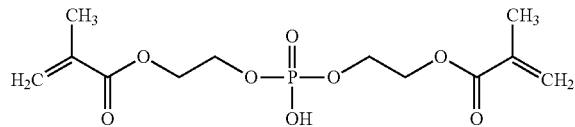 [SMILES: C=C(C)C(=O)OCCOP(=O)(O)OCCOC(=O)C(=C)C]

In one embodiment, BMEP may be between about 5-60 wt % of total weight of the dental bonding agent, such as 5 wt %, 10 wt %, 20 wt %, 25 wt %, 30 wt %, 35 wt %, 40 wt %, 50 wt %, 60 wt %, or a value between any two of the above values. In one embodiment, BMEP may be 10-40 wt %, or more preferably 20-40 wt %, and most preferably 30-35 wt %.

The amphiphile may contain hydrophilic groups (e.g. carboxyl groups or hydroxyl groups) as well as hydrophobic groups (e.g. acrylate groups). Examples of the amphiphile may include, but are not limit to, 2-hydroxyethyl methacrylate (HEMA), dipentaerythritol penta acrylate monophosphate (PENTA), N-phenylglycine glycidyl methacrylate (NPG-GMA), pyromellitic dianhydride (PMDA) and the like, which can be used alone or in combination. The hydrophilic groups of the amphiphile can crosslink with dentin tissue such as collagen fiber. Accordingly, the hydrophobic groups can react with the resin so that adhesion of the dentin and the resin may be achieved.

In one embodiment, the primer may comprise an amphiphile and a solvent. The solvent may have high volatility which facilitates removing water from dentin and resin entering into collagen fiber network. Preferably, the solvent contained in the dental bonding agent may have high volatility such as ethanol, propanol, isopropanol, acetone, or any combination thereof.

Optionally, the dental bonding agent of the present disclosure may further comprise an additional agent including initiators, accelerating agents, stabilizing agents, reinforcing agents and the like.

In some embodiments, the initiator may comprise benzoyl peroxide (BPO), acetyl peroxide, lauroyl peroxide (LP), camphorquinone (CQ) and the like, which can be used alone or in combination. In one embodiment, based on the total weight of the dental bonding agent, the initiator may be about 2 wt % or less, and more preferable about 1 wt % or less.

In one embodiment, an accelerating agent may be able to enhance the efficiency of the initiator-induced polymerization. The accelerating agent may comprise ethyl 4-dimethylaminobenzoate (EDMAB), N,N-dihydroxyethyl-p-toluidine (DHEPT) and the like.

In some embodiments, the dental bonding agent may comprise a stabilizing agent for longer storage. The stabilizing agent may comprise butylhydroxytoluene (BHT), hydroquinone and the like.

In some embodiments, the dental bonding agent may further comprise a reinforcing agent such as silanes. The reinforcing agent may be able to enhance the resin strength and reduce or eliminate microleakage caused by condensation polymerization of the resin materials.

The present disclosure may also provide a dental bonding agent for adhering dentin and an artificial post, which may comprise a composite resin composed of Bis-GMA and TEGDMA with a weight ratio of 1:1, BMEP having a ratio of 5-60 wt %, based on the total weight of the dental bonding agent, HEMA, and ethanol. In one preferred embodiment, the weight ratio of the composite resin:BMEP:HEMA:ethanol is 2:0.4-2.7:1:1.

In the dental bonding agent of the present disclosure, the composite resin may be comprised mainly of hydrophobic monomers. Bis-GMA and UDMA have high viscosity, so the addition of TEGDMA may be preferred to dilute and adjust the viscosity of the resin. In an acrylic resin, the frame network is formed by polymerization via two double-bonds of the acrylate group of a monomer, while the hydrophobic properties as well as the polymer strength are determined by the carried aromatic ring and the carbon content of the monomer. Accordingly, a stable hybrid layer may be formed by the smear layer and the dental bonding agent. Moreover, the amphiphile of the primer may cause the composite resin to extend into dentinal tubules to form resin tags. Accordingly, the adhesive strength may be further enhanced.

The dental bonding agent may be applied with a resin cement for crown restoration of root canal-treated teeth. The resin comment may be able to enhance post-dentin adhesion reliability. Further, the dental bonding agent may be applied with a simple and rapid operation.

The present disclosure further provides a coating agent that may comprise a composite resin, a primer comprising an amphiphile and at least one phosphate ester, a solvent, a pigment, and an inorganic filler. The coating agent of the present disclosure may be prepared by mixing the above dental bonding agent, a pigment, and an inorganic filler. The coating agent is harmless to the human body, can shade the discolored teeth, and provide color and gloss similar to natural teeth. Further, the coating layer of the teeth may not fall off during the meal and may be removed by toothbrush.

In one embodiment, the pigment may be selected from red pigment, yellow pigment, green pigment, blue pigment and the like, which may be used alone or in combination. For example, the red pigment may include Red Nos. 6, 7, 40 and the like; the yellow pigment includes Yellow Nos. 4, 5 and the like; the green pigment may include Green No. 3 and the like; the blue pigment may include Blue Nos. 1, 2 and the like. In one embodiment, based on the total weight of the coating agent, the ratio of the pigment may be about 0.1 wt % to about 5 wt %, such as 0.5, 1, 1.5, 2, 2.5, 3, 4, 4.5 wt %, or a value between any two of the above values.

In one embodiment, the inorganic filler may be selected from titanium dioxide, iron oxide, zinc oxide, aluminum oxide, chromium oxide, mica titanium, calcium oxide, magnesium oxide, tin oxide, hydroxyapatite, pearl, bismuth chloride oxide and the like, which may be used alone or in combination. In one embodiment, based on the total weight of the coating agent, the ratio of the inorganic filler is about 3 wt % to about 25 wt %, such as 3, 5, 7, 10, 15, 20, 22, 25 wt %, or a value between any two of the above values.

Examples of the bonding agent and the coating agent are further described hereafter.

EXAMPLES

Example 1

Dental Bonding Agent (A) Preparation Example

Materials

Bis-GMA, TEGDMA, CQ, ethanol (≥99.5%), BMEP, and HEMA were purchased from Sigma-Aldrich (St. Louis, Mo., USA) and used without further purification. TEGDMA and EDMAB were purchased from Wako Pure Chemical Industries, Ltd. (Japan). IBOA, EHA, 1,6-hexanediol diacrylate (HDDA), and tripropylene glycol diacrylate (TPGDA) were purchased from Double Bond Chemical (Taipei, Taiwan) and used without further purification. BPO was purchased from Alfa Aesar GmbH & Co KG.

1. Preparation of Resin Matrix

TEGDMA was added into Bis-GMA (weight ratio: 1:1) in warm water bath, and stirred to homogenously mix. The mixture was placed under 4° C. for 24 hours to eliminate bubbles which may not be observed by naked eyes. The mixture was stored in 4° C. until use.

2. Preparation of Resin Cement

The resin cement (hereafter "IE" or "IE cement") was prepared by adding IBOA and EHA into the above resin matrix.

A flask was covered by aluminum foil, the ingredients with the ratio of the resin matrix/EDMAB/BPO/CQ: 1/0.005/0.005/0.0025 were mixed with dual initiators and stirred. 5 wt % of cIBOA and 5 wt % of cEHA (cIBOA=50% IBOA+25% HDDA+25% TPGDA, and cEHA=50% EHA+25% HDDA+25% TPGDA) were then added, and stirred to homogenously mix. The mixture was placed under 4° C. for 24 hours to eliminate bubbles which may not be observed by naked eyes. The mixture was stored in 4° C. until use.

3. Preparation of Dental Bonding Agent

The dental bonding agent was prepared by adding ethanol, HEMA, and various concentrations of BMEP into the above resin matrix.

A flask was covered by aluminum foil, the ingredients with the ratio shown in Table 1 were added with dual initiators and mixed homogeneously. The mixture was placed under 4° C. for 24 hours to eliminate bubbles which may not be observed by naked eyes. The mixture was stored in 4° C. until use.

TABLE 1

| Group | Weight ratio of resin matrix/HEMA/BMEP/ethanol |
|---|---|
| BMEP (10%) | 2/1/0.4444/1 + initiator |
| BMEP (20%) | 2/1/1/1 + initiator |
| BMEP (25%) | 2/1/1.3333/1 + initiator |
| BMEP (30%) | 2/1/1.7143/1 + initiator |

TABLE 1-continued

| Group | Weight ratio of resin matrix/HEMA/BMEP/ethanol |
|---|---|
| BMEP (35%) | 2/1/2.1538/1 + initiator |
| BMEP (40%) | 2/1/2.6667/1 + initiator |

*initiator: EDMAB + BPO + CQ
* Weight ratio of initiator: (resin matrix/HEMA/BMEP/ethanol)/EDMAB/BPO/CQ = 1/0.005/0.005/0.0025

(B) Test Example

1. Adhesive System

Six adhesive systems were used in the Test Examples.

(1) BMEP dentin bonding agent of the present disclosure with IE cement (hereafter "BMEP system"). Various concentrations of BMEP, i.e. 10%, 20%, 25%, 30%, 35%, and 40%, were tested.

(2) Optibond bonding agent (purchased from Kerr CORP.) with IE cement.

(3) NX3 (purchased from Kerr CORP.): total etching system. An etchant is essential. Its bonding agent is Optibond Solo Plus.

(4) Variolink II (purchased from Ivoclar Vivadent): total etching system. An etchant is essential. The product contains Paste A and Paste B (volume ratio: 1:1), and Primer Excite DSC.

(5) RelyX Unicem (purchased from 3M/ESPE): self-etching system. The cement is directly applied on teeth, and the operation steps were referred to the manufacture's instruction.

(6) Panavia F (purchased from Kuraray): self-etching system. The product contains Paste A and Paste B (vol. ratio: 1:1), and ED Primer.

The above adhesive systems (2)-(5) are commercial products. Detail information was shown in Table 2.

TABLE 2

|  | BMEP system | Optibond | NX3 | Variolink II | RelyX Unicem | Panavia F |
|---|---|---|---|---|---|---|
| Gel Etchant | 37.5% $H_3PO_4$ | 37.5% $H_3PO_4$ | 37.5% $H_3PO_4$ | 37.5% $H_3PO_4$ | — | — |
| Bonding agent | BMEP | Optibond Solo Plus | Optibond Solo Plus | Excite DSC | — | ED primer |
| Cement | IE | IE | NX3 | Variolink II | RelyX Unicem | Panavia F |

*Gel Etahant: purchased from Kerr CORP., Lot#4437996.

2. Tests

The adhesive strength of these adhesive systems to coronal and root canal dentin was tested using a microtensile bond test, push-out bond test, and fracture toughness test. Attenuated total reflectance-Fourier transforming infrared spectroscopy (ATR-FTIR) and X-ray photoelectron spectroscopy (XPS) were employed to analyze the surfaces following the fracture toughness test to identify the failure location.

(1) Microtensile Bond Test

Thirty-six human molars without dental caries or fractures were used for this test. Any remaining soft tissue was removed from the tooth surfaces by using a dental scaler (Sonicflex 2000, KaVo Co, Biberbach, Germany) under running water. All teeth were stored in distilled water containing 0.2% thymol at 4° C. to inhibit microbial growth and the storage medium was replaced every week to minimize deterioration. All preserved specimens were bond tested within 1 month.

While fully hydrated, each molar was cut using a low-speed diamond wafering blade (Isomet, Buehler Ltd, Lake Bluff, Ill., USA) immediately below the occlusal pit and fissure, perpendicular to the long axis of the tooth. The dentin surfaces were subsequently wet-polished using 600 grit silica paper to create a uniform flat surface, followed by sonic vibration in distilled water for 30 seconds to remove any superficial debris caused by the cutting and polishing procedures. 36 molars were randomly divided into 12 groups with 3 molars in each group.

Kerr Gel Etchant (37.5% phosphoric acid) was applied to etch the dentin surface for 15 seconds before thoroughly rinsing and air-drying them. The BMEP system of the present disclosure was subsequently applied for 15 seconds before using absorbent paper points to remove the excess adhesive. A light-curing machine (SmartLite, Dentsply, Pa., USA) was then used to light cure the surfaces for 10 seconds with a light intensity of 800 mW/cm$^2$. Subsequently, the dentin surface was encircled with a plastic ring (7 mm in diameter) and filled with an adequate amount of the IE cement before light cure for 40 seconds. The specimens were then placed in 100% relative humidity at 37° C. for 24 hours.

Optibond Group and NX3 Group were treated as the same procedures for BMEP Group. Variolink II, RelyX Unicem, and Panavia F Groups were processed according to the manufacture's instructions, respectively.

Each specimen was sectioned into multiple 1.0×1.0 mm beams by using a low-speed saw (Isomet, Buehler Ltd, Lake Bluff, Ill., USA) under water cooling. Microtensile Bond Test was performed by using microtensile testing machine (Microtensile Tester, Bisco, Inc, Schaumburg, Ill., USA).

The test results are shown in FIG. 1, the microtensile bond strength of Optibond, BMEP (0%), BMEP (10%), BMEP (20%), BMEP (25%), BMEP (30%), BMEP (35%), BMEP (40%), NX3, Variolink II, Unicem and Panavia F was 34.17 MPa, 0 MPa, 8.45 MPa, 34.16 MPa, 36.66 MPa, 38.62 MPa, 34.53 MPa, 34.19 MPa, 30 MPa, 29.23 MPa, 17.03 MPa and 14.27 MPa, respectively. In the test results, BMEP (30%) had the best strength (i.e. 38.6±2.5 MPa) with significant difference with other groups (P<0.05). Optibond, BMEP (20%), BMEP (25%), BMEP (35%), and BMEP (40%) belonged to the second best strength, and the difference of the test results between these groups were insignificant (P>0.05). NX3 and Variolink II belonged to the third best strength, and the difference of the test results between these groups were insignificant (P>0.05). Unicem, Panavia F, BMEP (10%), and BMEP (0%) had the lowest microtensile bond strength, and the difference of the test results between these groups were significant.

One of ordinary skill in the art would appreciate that, according to the test results, the binding between BMEP and coronal dentin was affected by BMEP concentration. The preferred BMEP concentration for coronal dentin was 30% of the total weight of the dentin bonding agent. The groups of BMEP (35%) and BMEP (40%) had insignificant statistical difference in microtensile bond strengths (P=0.762). Regarding the commercial adhesive system, NX3 and Variolink II had better adhesion than the remaining groups. Panavia F showed the worst adhesion (14.27 MPa), i.e. about a half of the microtensile bond strength of other groups.

(2) Push-Out Bond Test

The palatal roots of the maxillary molars or distal roots of mandibular molars were used to perform a push-out bond strength test. The distal roots of mandibular molars that had 2 root canals were excluded from this test. The apical portion of each root (approximately 3 mm) was cut away to obtain a 9 mm root sample. Each canal was prepared until the apical opening could be passed using an ISO size 80, 0.02 taper file. The prepared root specimen was vertically restrained using an apparatus comprising 2 aligned cylindrical steel dies secured with 3 screws. Under copious distilled water cooling, a multi-drilling machine (LT-848; Dengyng Instruments Co Ltd, Taipei, Taiwan) was used to drill a 1.8 mm diameter hole along the center of the root canal of each specimen. The drilled canals were at least 1 mm away from the edge of the specimen.

A custom-made alignment device was employed to mount each prepared root vertically in a custom-made aluminum cylinder (3 cm diameter, 2 cm height). The aligning device contained a base plate with 3 orientation screws and 1 central guiding pin. Each prepared root was first positioned in the cylinder using the central guiding pin. After a thin layer of petroleum jelly was applied to the inner wall of the cylinder, the root was embedded by pouring a self-curing acrylic resin (Tempron; GC Corp, Tokyo, Japan) into the space between the fringe of the root and the cylinder wall. The cylinder was removed after the acrylic resin had set and a resin block with a mounted root segment was obtained. All specimens were immersed in an ultrasonic cleaner (Delta; Mandarin Scientific Co Ltd, Taipei, Taiwan) filled with 2.5% NaOCl for 1 min, followed by 17% EDTA for 2 min to remove the smear layer, and finally in distilled water for 2 min.

Thirty-six resin blocks were randomly divided into 9 groups with 4 blocks in each group. Treatment of the canals in the root segments was identical to the above steps of adhesive system-dentin treatment for the microtensile tests. Subsequently, the top and bottom surfaces of the root segment were then light-cured for 40 second each with a light intensity of 800 mW/cm$^2$. The root segment was then placed in 100% relative humidity at 37° C. for 24 hours.

Each block was then serially sectioned to create 1-mm root slices by using a high-speed diamond wafering blade (Isomet 2000 Precision High-Speed Saw; Buehler Ltd). The push-out bond strength tests was performed by universal testing machine (Merlin series, Mini-55; Instron Corp., Canton, Mass.), and the parameters included: crosshead speed of 0.5 mm/sec, critical value of load of 500N, sensitivity of 40%, processing of "compression extension control." Maximum push-out strength (N), distance (mm) and time (sec) were detected and calculated to interfacial shear stress (ISS) in MPa unit based on the conventional formula.

Figure 2:
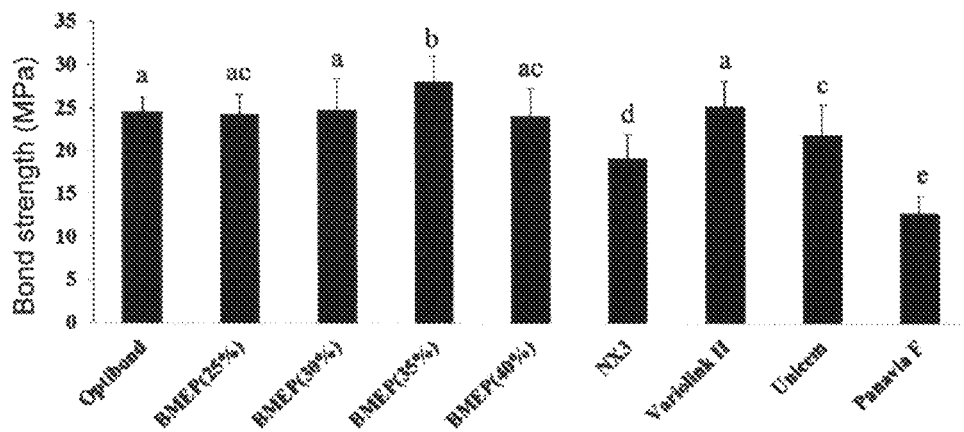
FIG. 2 illustrates push-out bond test results.

The test results are shown in FIG. 2, the push-out bond strength of Optibond, BMEP (25%), BMEP (30%), BMEP (35%), BMEP (40%), NX3, Variolink II, Unicem and Panavia F was 24.63 MPa, 24.22 MPa, 24.69 MPa, 28.0 MPa, 24.04 MPa, 19.12 MPa, 25.18 MPa, 21.86 MPa, and 12.71 MPa, respectively. Accordingly, BMEP (35%) had the best strength (i.e. 28.0 MPa) with significant difference with other groups (P<0.05), while Optibond, BMEP (25%), BMEP (30%), BMEP (40%) and Variolink II belonged to the second best strength with insignificant difference with other groups (P<0.05). Unicem, NX3, Panavia F had the lowest strength, and the significant difference were with other groups (P<0.05) except Unicem and BMEP (40%) or BMEP (25%) (P=0.088).

One of ordinary skill in the art would appreciate that, based on the test results, the preferred BMEP concentration for the push-out bond strength test was 35% of the total weight of the dentin bonding agent. The push-out bond strength was affected by increased or reduced BMEP concentration. One of ordinary skill in the art would appreciate that the test results indicate that the bonding agent suitable for coronal dentin and root canal dentin contained different BMEP concentrations.

Regarding the commercial adhesive system, Variolink II with 25.18 MPa of strength was the preferred one while Panavia F was the worst one.

(3) Fracture Toughness Test

Extracted permanent teeth with single roots longer than 25 mm were used to perform the fracture toughness test. A total of 80 specimens were prepared from root dentin (25 mm×4 mm×2 mm) and randomly divided them into 8 groups with 10 specimens in each group. Resin cements were also prepared (25 mm×4 mm×3 mm). The remaining surface treatments are identical to those of the push-out bond strength test. The interfacial fracture toughness (Gc) between the resin cement and dentin was measured using an asymmetric double cantilever beam (ADCB) method. A razor blade driven by a servo motor at a constant speed ($5 \times 10^{-6}$ m/s) was inserted into the dentin/resin cement interface. A crack was initiated ahead of the razor edge. Steady state crack propagation was observed after several minutes. The length of the crack was detected per 10 seconds, the means of the crack length was used to calculate Gc value based on conventional formula.

Figure 3:
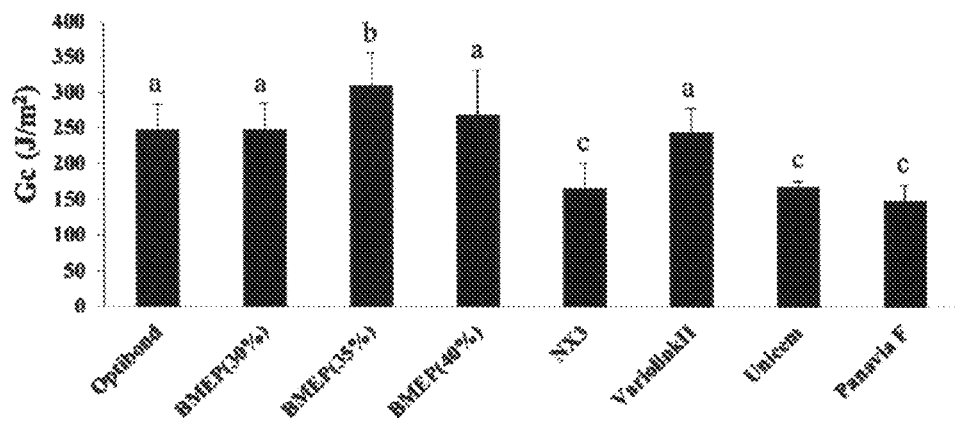
FIG. 3 illustrates fracture toughness test results.
Figure 4A:
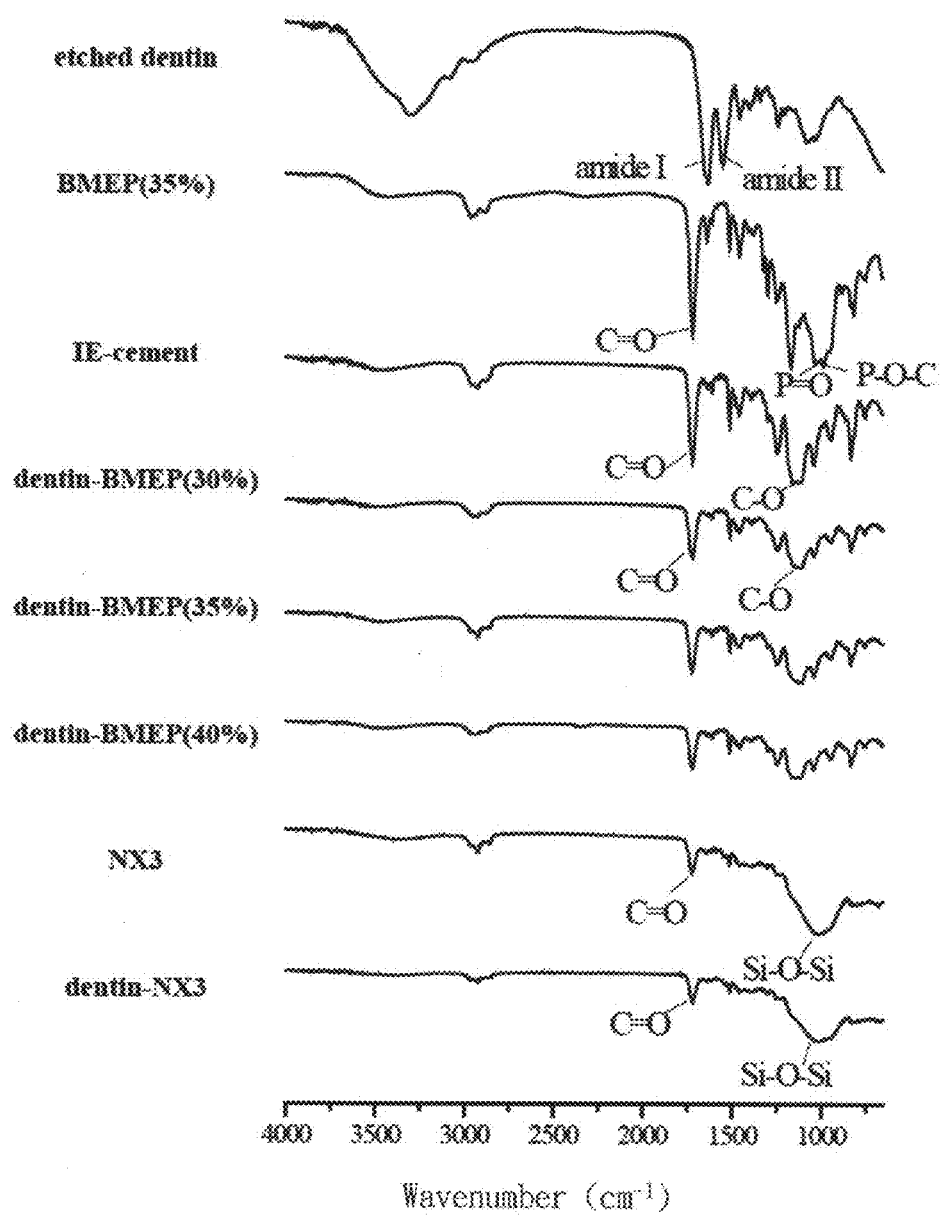
FIG. 4A illustrates an ATR-FTIR spectra.
Figure 4B:
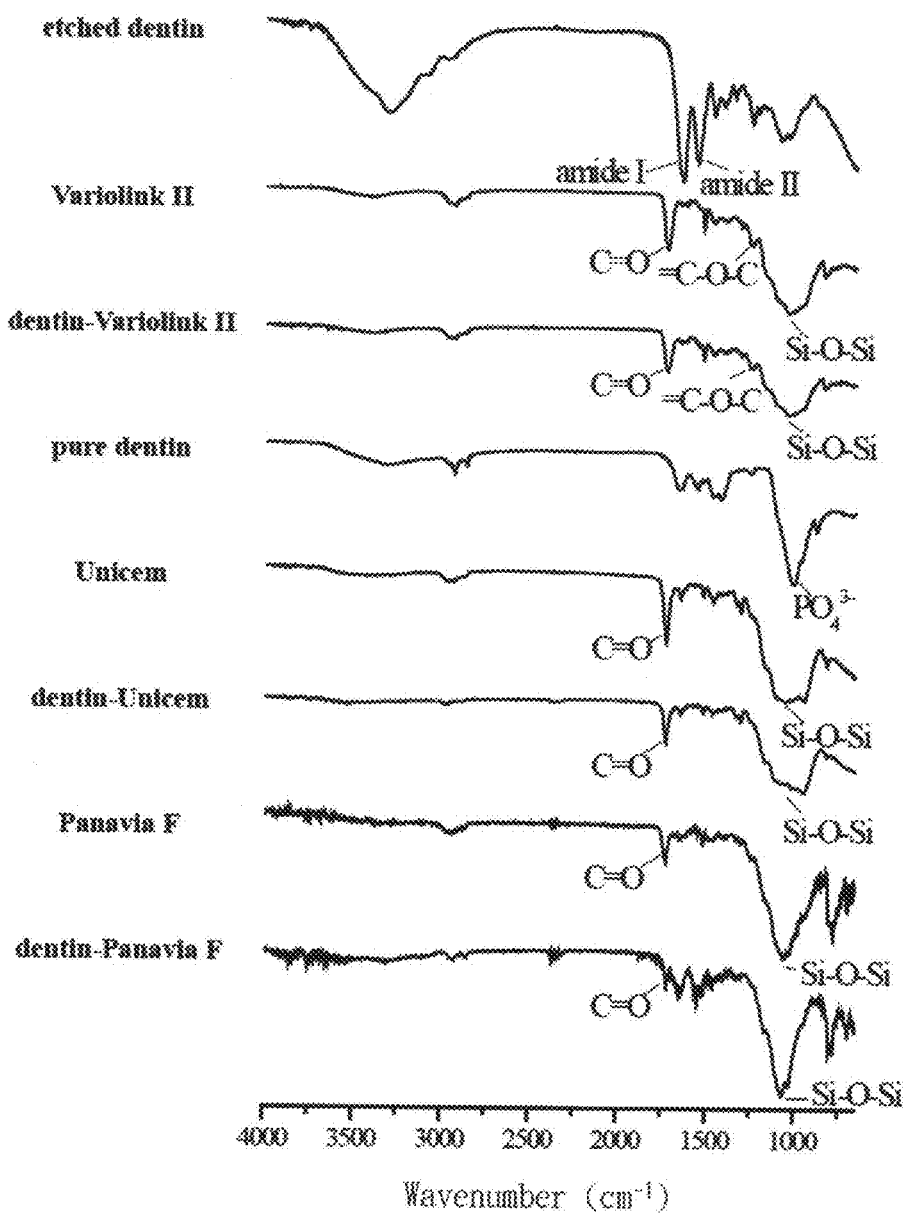
FIG. 4B illustrates an ATR-FTIR spectra.
Figure 5A:
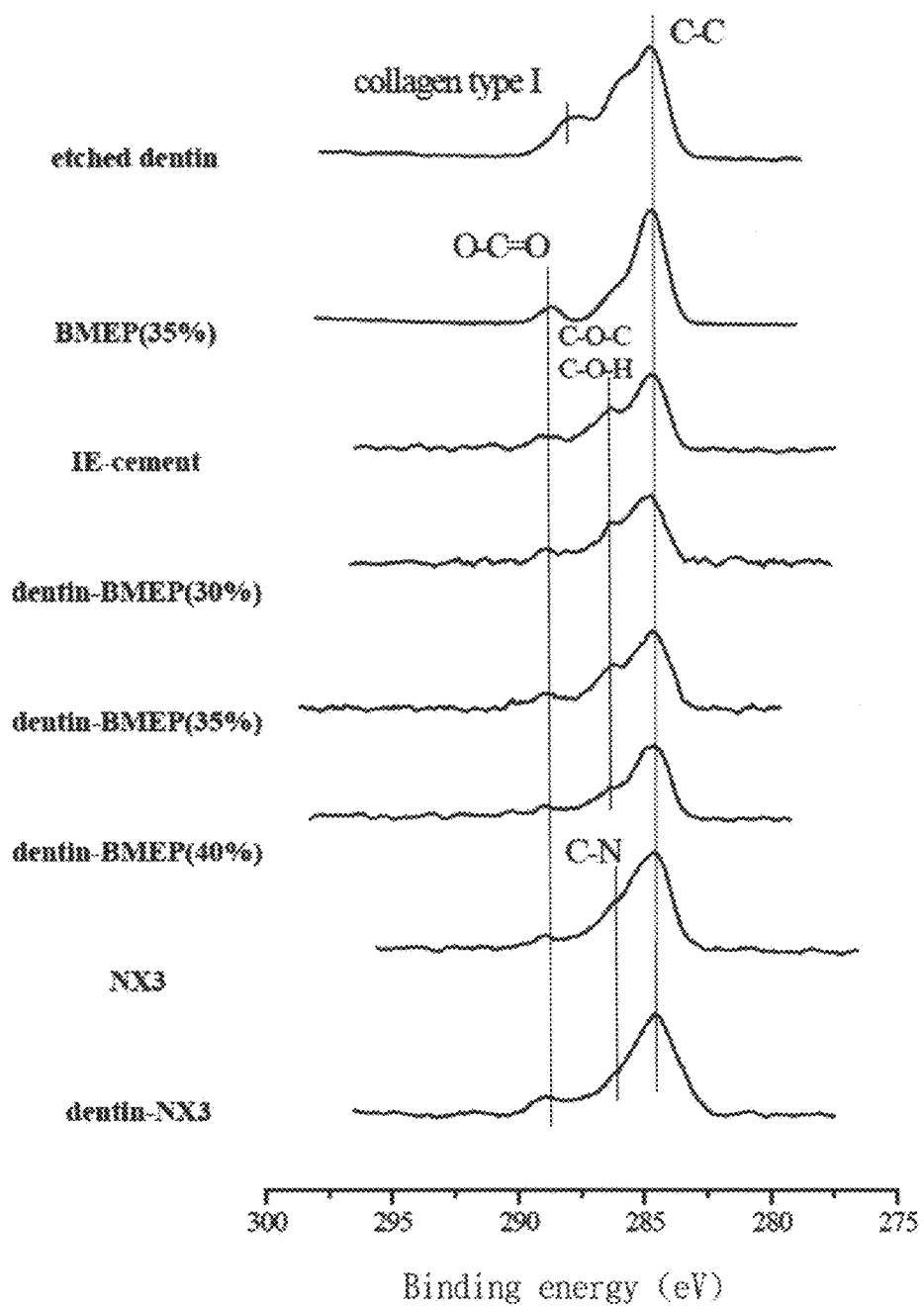
FIG. 5A illustrates an XPS spectra.
Figure 5B:
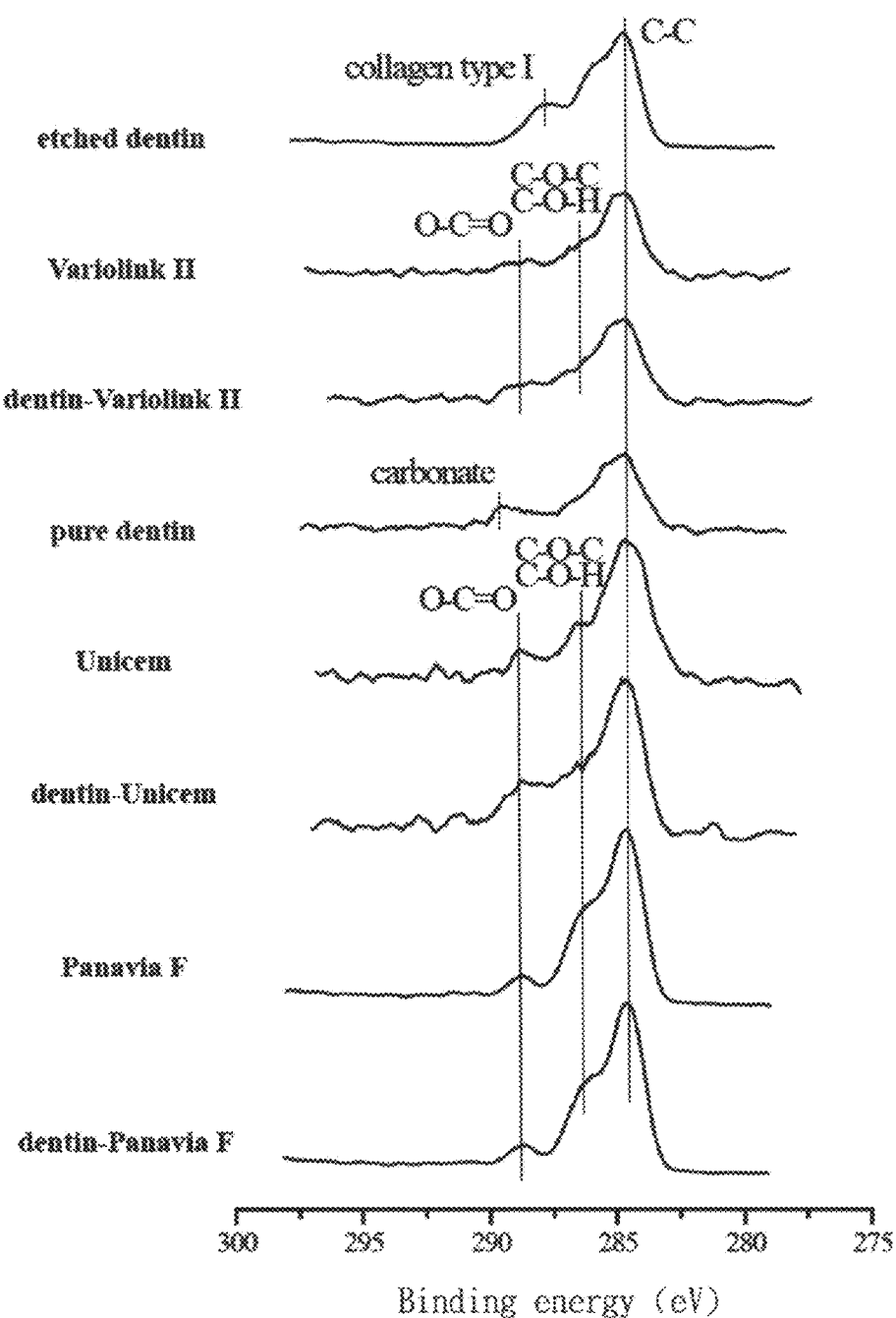
FIG. 5B illustrates an XPS spectra.

The test results are shown in FIG. 3, the fracture toughness test of Optibond, BMEP (30%), BMEP (35%), BMEP (40%), NX3, Variolink II, Unicem and Panavia F was 247.13 $J/m^2$, 248.04 $J/m^2$, 309.8 $J/m^2$, 269.45 $J/m^2$, 167.47 $J/m^2$, 244.63 $J/m^2$, 169.05 $J/m^2$, and 148.44 $J/m^2$, respectively. BMEP (35%) showed the best fracture toughness with dentin, i.e. 309.8 $J/m^2$. BMEP (40%), BMEP (30%), Variolink II and Optibond were the second best with insignificant difference with each other. Unicem, NX3 and Panavia F were the third best with insignificant difference.

Root canal dentin was used for the fracture toughness test as well as push-out bond strength test, so that the results of the above two tests should be consistent in theory. One of ordinary skill in the art would appreciate that the results of the above two tests were generally consistent, i.e. BMEP (35%) was the group with the best result, then followed by BMEP (30%), Variolink II and BMEP (40%) with insignificant difference in the three groups, and Unicem, NX3, and Panavia F were the worst groups. Although there were statistically significant differences from the results of the two tests, Unicem, NX3, and Panavia F were appreciably the worst groups, especially Panavia F.

(4) Detection of Residual Resin Cement

Following the fracture toughness test, the fractured surfaces of dentin/resin cement samples were examined using ATR-FTIR (FT/IR-4200, Jasco International Co., Ltd., Tokyo, Japan). The test samples included dentin half (dentin/resin cement samples), pure resin cement, pure dentin slice with acid etchant treatment, and pure dentin slice without any treatment. The test results are shown in FIGS. 4A-4B and 5A-5B.

In FIG. 4, most spectra had bands at 3200-3400 $cm^{-1}$ representing —NH and —OH, which included water absorption from air. In spectrum of the untreated dentin slice, the bands represented functional groups including v3 $PO_4^{3-}$ (955 $cm^{-1}$), v1 $PO_4^{3-}$ (1010 $cm^{-1}$), amide I (1640 $cm^{-1}$), amide II (1540 $cm^{-1}$), v3 $CO_3^{2-}$ (1410 $cm^{-1}$, 1450 $cm^{-1}$) and v1 $CO_3^{2-}$ (870 $cm^{-1}$). After acid etching was performed, the dentin surface was demineralized to expose collagen, thus the strong collagen bands representing amide I (1640 $cm^{-1}$), amide II (1540 $cm^{-1}$), and amide III (1240 $cm^{-1}$) expressed or increased while the bands of $PO_4^{3-}$ (955 $cm^{-1}$, 1010 $cm^{-1}$) and $CO_3^{2-}$ (870 $cm^{-1}$) reduced or disappeared because of removal of phosphoric acid and carbonic acid.

The pure IE-cement was mainly composed of acrylates. Thus, its spectrum contained bands of C=O (1716 $cm^{-1}$), $CH_2$—$CH_3$ (1457 $cm^{-1}$), C—O stretching (1165 $cm^{-1}$), and C—C—O (832 $cm^{-1}$). Further, other resin-relevant bands including =C—O—C (1230-1270 $cm^{-1}$), =CH—OH (1085-1125 $cm^{-1}$), and —C—O—C (1060-1150 $cm^{-1}$). All of the dentin half of BMEP (30%), BMEP (35%), and BMEP (40%) had the bands of the same functional groups.

The groups subjected acid etching included BMEP (30%), BMEP (35%), BMEP (40%), NX3, and Variolink II. The spectra of these groups were distinct from those of the acid-etched pure dentin but identical to that of pure IE-cement. Specifically, the resin cements remained on the dentin half. The groups without treatment of acid etching, Unicem and Panavia F, showed the same results. Their spectra were distinct from that of the acid-etched pure dentin but identical to that of pure IE-cement. That is, all adhesive systems showed the same results, i.e. resin cement was remained on dentin half. Further, the spectra of BMEP (30%), BMEP (35%), and BMEP (40%) were distinct from that of the dentin half. Accordingly, one may exclude the possibility that the fracture was along the interface between the bonding agent and the dentin.

In FIG. 5, the peak of carbon-carbon single bond (C—C, 284.6 eV) existed in all groups. The spectrum of the untreated dentin contained, in addition to the peak of C—C single bond (284.6 eV), a peak of carbonate radical (289.5 eV) which replaces the phosphate radical of hydroxyapatite. After acid etching was performed, the dentin surface was demineralized to expose collagen and lose carbonate radical, so that the band 289.5 eV disappeared and the collagen type I relevant band (N—C=O, 287.5 eV) appeared.

The spectra of the pure IE-cement, Variolink II, Unicem, and Panavia F contained, in addition to the peak of C—C single bond (284.6 eV), the peaks of C—O single bond (C—O—C, C—O—H, 286.5 eV) and C—O double bond (O—C=O, 289.5-288.4 eV), which were from methyl acrylic resins (Bis-GMA, TEGDMA). The above peak also existed in the spectra of dentin half of BMEP (30%), BMEP (35%), BMEP (40%), Variolink II, Unicem, and Panavia F. In NX3 group, the peaks of C—O double bond (O—C=O, 288.75 eV) and C—N single bond (C—N, 286 eV) from urethane dimethacrylate (UDMA) also appeared.

The spectra of the groups subjected to acid etching included BMEP (30%), BMEP (35%), BMEP (40%), NX3, and Variolink II were distinct from those of the acid-etched pure dentin but identical to those of pure IE-cement. Specifically, the resin cements were remained on the dentin half. The groups without treatment of acid etching, i.e. Unicem and Panavia F, showed the same results. Their spectra were distinct from that of the acid-etched pure dentin but identical to that of pure IE-cement. The ATR-FTIR detection result was consistent to the XPS detection result. That is, all adhesive systems showed that resin cement remained on the dentin half.

Further, all of the spectra of BMEP (30%), BMEP (35%), and BMEP (40%) had C—O double bond (O—C=O, 289.5-288.4 eV). However, the bonding agents had no C—O single bond peaks (C—O—C, C—O—H, 286.5 eV) on the fractured dentin half. Accordingly, one may exclude the possibility that the fracture was along the interface between the bonding agent and the dentin.

Dentin is a biological component having hydrophilic properties. As one of ordinary skill in the art would appreciate, the hydrophilic properties make dentin incompatible with cements. Therefore, the interface of dentin and dental cement should be considered. In the embodiments the present disclosure, Bis-GMA and TEGDMA are used as a resin matrix and mixed with HEMA, ethanol, and various concentration of BMEP. The dental bonding agent can then be prepared by polymerization of the above ingredients induced by dual initiator.

Based on the test results of binding strength between the dental bonding agent and dentin, the addition of 20-40% of BMEP significantly improves the bond strength. More specifically, the addition of 35% of BMEP is preferred. In clinical application, the dental bonding agent is used in root canal. Push-out bond test and fracture toughness test of root canal confirm that the BMEP bonding agent of the present disclosure significantly enhances the bond strength (i.e. the results of 35% of BMEP are 28.0 MPa and 309.8 J/m$^2$), which is better than the conventionally commercial dentin adhesive systems.

A part of the IE-cement still remains on the dentin after the fracture toughness test. One of ordinary skill in the art would appreciate that these results indicate that the BMEP bonding agent is able to enhance the resin cement-dentin binding. Further, the bond strength between the BMEP bonding agent and dentin is higher than that of polymerization of the bonding agent.

According to the above, the dental bonding agent of the present disclosure advantageously improves the adhesive reliability between the root canal dentin and the artificial post or the resin cement. The dental bonding agent of the present disclosure can be applied to crown restoration of root canal-treated teeth with simple and rapid operation.

Example 2

Dental Coating Agent (A) Preparation Example

A flask was covered by aluminum foil. Ingredients with the ratio shown in Table 3 were mixed with dual initiators and stirred homogeneously. Then, the inorganic filler or the pigment was added. The mixture was placed under 4° C. for 24 hours to eliminate bubbles which may not be observed by naked eyes. The mixture was stored in 4° C.

Type and ratio of the inorganic filler determines the shading ability, color, or particle dispersion. For example, the more TiO$_2$ present, the more shading ability. However, a coating agent containing too much filler may be too thick to be coated. Iron oxide (representing red, yellow, or black) was used to adjust the color of the dental coating agent.

TABLE 3

| Group | Weight ratio of resin matrix/ HEMA/BMEP/ethanol |
|---|---|
| BMEP(10%) | 2/1/0.4444/1 + initiator + filler |
| BMEP(20%) | 2/1/1/1 + initiator + filler |
| BMEP(25%) | 2/1/1.3333/1 + initiator + filler |
| BMEP(30%) | 2/1/1.7143/1 + initiator + filler |
| BMEP(35%) | 2/1/2.1538/1 + initiator + filler |

*initiator: EDMAB + BPO + CQ
* Weight ratio of initiators: (resin matrix/HEMA/BMEP/ethanol)/EDMAB/BPO/CQ = 1/0.005/0.005/0.0025
* filler: TiO$_2$ + SiO$_2$ + ZnO + iron oxide
* Weight ratio of fillers: (resin matrix/HEMA/BMEP/ethanol/initiator)/TiO$_2$/SiO$_2$/ZnO/iron oxide = 1/0.13/0.05/0.05/0.001

(B) Test Example

1. The Coating Agent

Six formulations were tested and applied to human anterior teeth and four types of fuscous artificial resin teeth: A4, B4, C4, and D4 (VITA classical Shade Guide). The bonding agents containing 10%, 20%, 25%, 30%, or 35% BMEP were prepared. The same ratio of the filler was added to prepare the coating agent. The adhesive property and the shading ability of the coating agents were observed.

2. Tests

Tests of adhesive property and shading ability of the above six coating agents were performed. Regarding the adhesive test, human teeth were coated by the coating agent, and removal of the coating layer by toothbrush was observed to evaluate the adhesive property of the coating agent. Regarding the shading test, the artificial resin teeth were coated by the coating agent, then the shading ability and the alteration of teeth appearance were evaluated.

(1) Adhesive Test

Preparation of Test Sample:

Human incisors without dental caries or fracture were used for this test. The coating agent as shown in Table 3 was uniformly coated on the crown surface by using a brush. Polymerization was induced by applying halogen light for 50 seconds. The coating and polymerization steps were repeated to form a glossy and uniform coating layer on enamel surface.

Figure 6A:
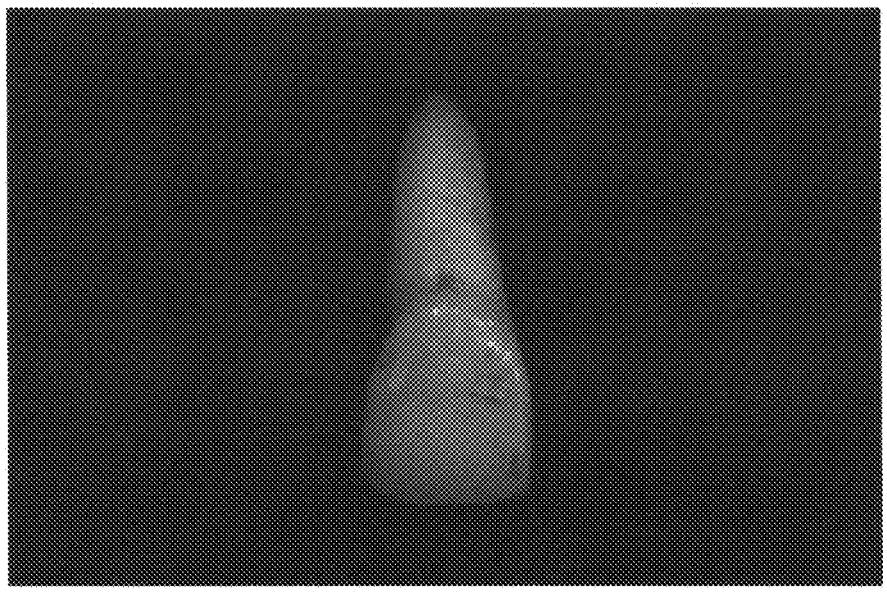
FIG. 6A illustrates test results of human anterior teeth before application of the coating agent of the present disclosure.
Figure 6B:
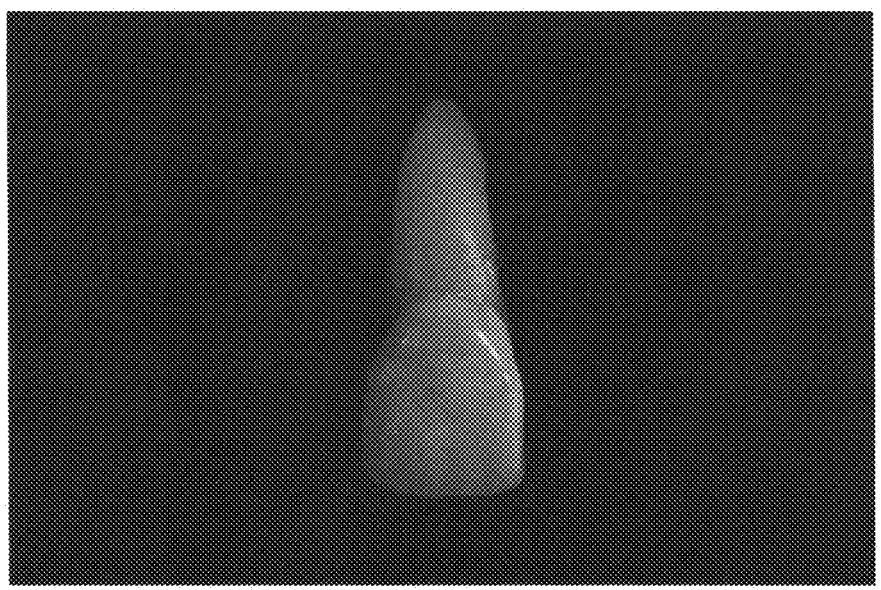
FIG. 6B illustrates test results of human anterior teeth after application of the coating agent of the present disclosure.

Routine oral cleaning was applied by using a toothbrush to brush the crown without toothpaste. The removal of the coating layer was observed. The test results are shown in Table 4 and FIG. 6.

In the six examples, it was easiest to remove the coating layers of the groups BMEP (0%) and BMEP (10%), then the groups BMEP (20%) and BMEP (25%). The groups BMEP (30%), BMEP (35%) were the hardest groups to be removed by toothbrush. All examples could be scraped mechanically.

BMEP concentration affected the binding with enamel surface of the crown. Based on the test results, the preferred concentration of BMEP in the coating agent was 0%-10%. The prepared coating agent can be removed by toothbrush to avoid adverse effects to oral health.

TABLE 4

| Group | Adhesive result* |
|---|---|
| BMEP (0%) | 1 |
| BMEP (10%) | 1 |
| BMEP (20%) | 2 |
| BMEP (25%) | 3 |
| BMEP (30%) | 4 |
| BMEP (35%) | 4 |

1: complete removal
2: slight remaining
3: remaining half of the coating layer
4: remaining more than half of the coating layer.

(2) Shading Test

Figure 7A:
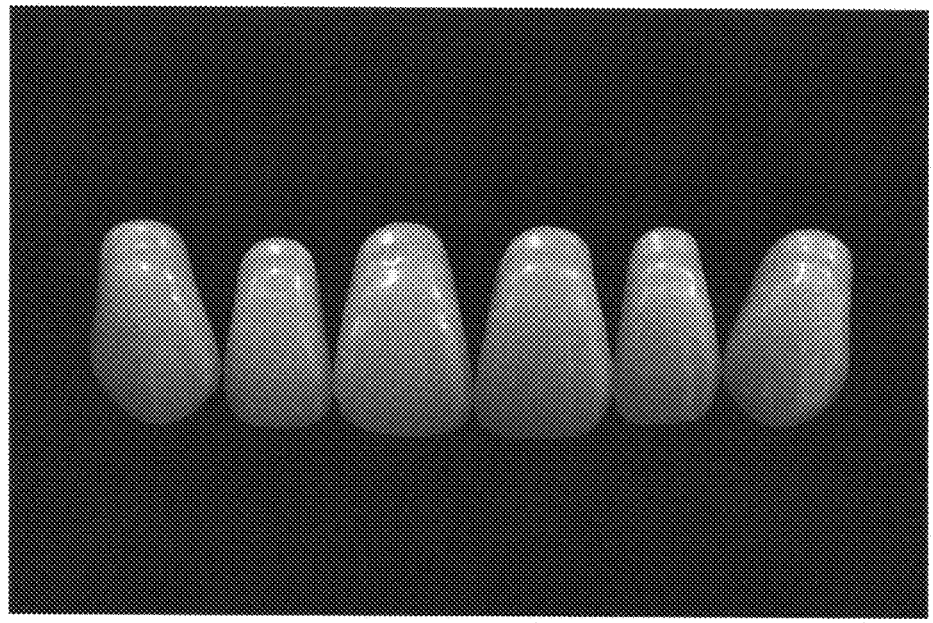
FIG. 7A illustrates the shading test results of artificial A4 red-brown resin anterior teeth before application of the coating agent of the present disclosure.
Figure 7B:
FIG. 7B illustrates the shading test results of artificial A4 red-brown resin anterior teeth after application of the coating agent of the present disclosure.
Figure 7C:
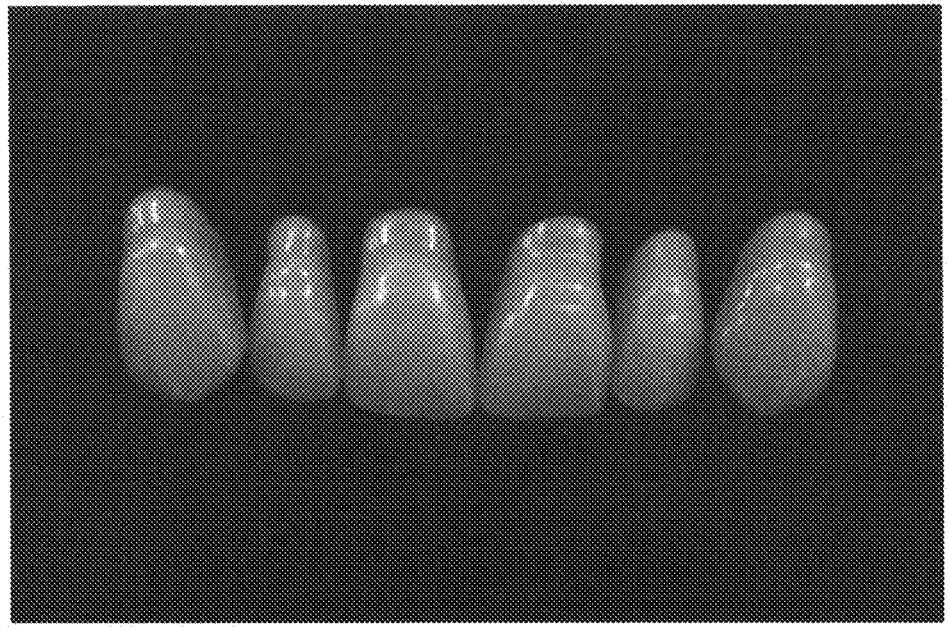
FIG. 7C illustrates the shading test results of artificial B4 red-yellow resin anterior teeth before application of the coating agent of the present disclosure.
Figure 7D:
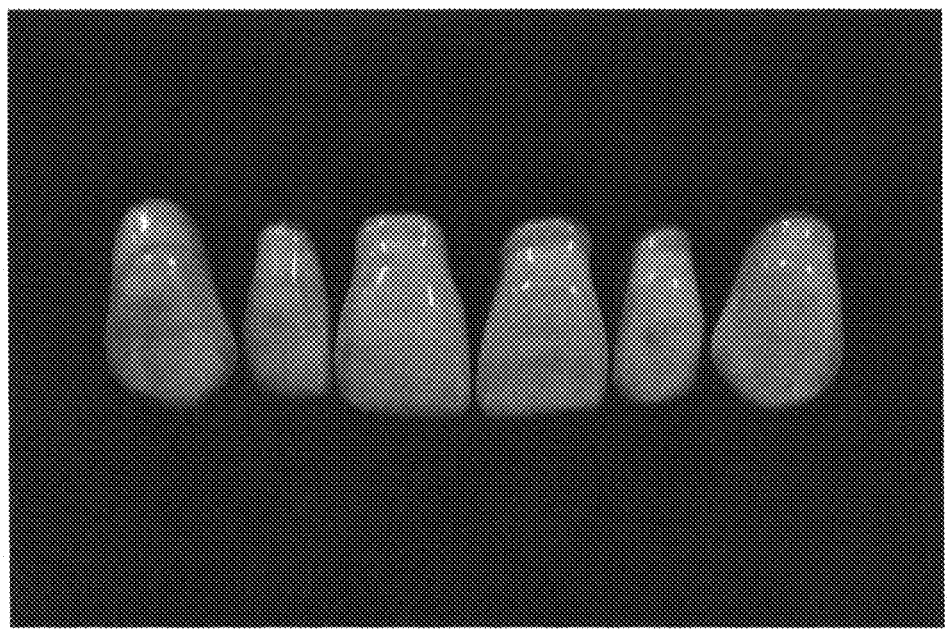
FIG. 7D illustrates the shading test results of artificial B4 red-yellow resin anterior teeth after application of the coating agent of the present disclosure.
Figure 7E:
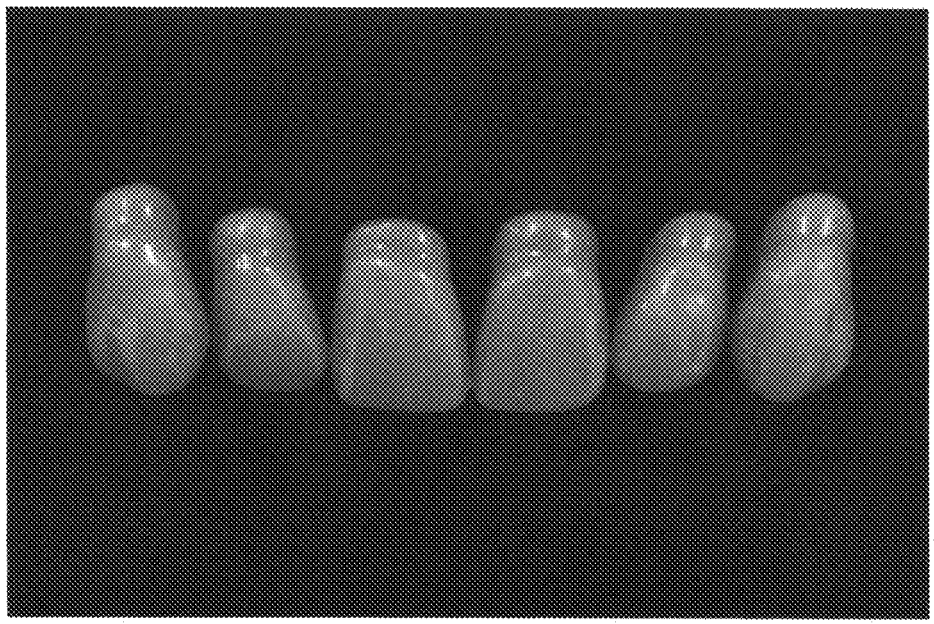
FIG. 7E illustrates the shading test results of artificial C4 gray resin anterior teeth before application of the coating agent of the present disclosure.
Figure 7F:
FIG. 7F illustrates the shading test results of artificial C4 gray resin anterior teeth after application of the coating agent of the present disclosure.
Figure 7G:
FIG. 7G illustrates the shading test results of artificial D4 red-gray resin anterior teeth before application of the coating agent of the present disclosure.
Figure 7H:
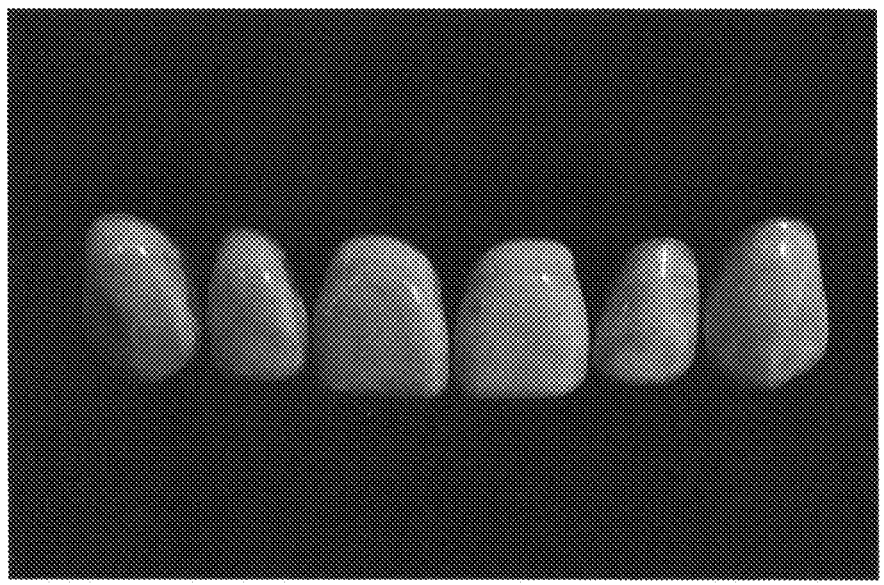
FIG. 7H illustrates the shading test results of artificial D4 red-gray resin anterior teeth after application of the coating agent of the present disclosure.

Four types of resin anterior teeth: A4, B4, C4, and D4 (VITA classical Shade Guide) were used, and each type had 6 teeth. The coating agent was uniformly coated on the crown surface by using a brush. Polymerization was induced by applying halogen light for 50 seconds. The coating and polymerization steps were repeated to form a glossy and uniform coating layer on enamel surface. The photographs showed the coating results, i.e. A4: red-brown resin teeth (FIG. 7A, B), B4: red-yellow resin teeth (FIG. 7C, D), C4: gray resin teeth (FIG. 7E, F), and D4: red-gray resin teeth (FIG. 7G, H). All teeth were shaded well and had natural gloss. One of ordinary skill in the art would appreciate that the results indicate that the coating agent of the present disclosure is able to beautify the color of seriously yellowed teeth and/or shade the spots on teeth. Depending on requirements of beauty, the color and the transparency of the coating agent can be adjusted by the type and ratio of the filler.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the disclosure and the scope of the following claims and its equivalent systems and methods.

What is claimed is:

1. A dental bonding agent for adhering dentin and an artificial post comprising:
    a composite resin composed of bisphenol A glycerolate dimethacrylate (Bis-GMA) and triethylene glycol dimethacrylate (TEGDMA) with a weight ratio of 1:1;
    bis[2-(methacryloyloxy)-ethyl]phosphate (BMEP) having a ratio of 20-40 wt %, based on the total weight of the dental bonding agent;
    2-hydroxyethyl methacrylate (HEMA); and
    ethanol.

2. The dental bonding agent of claim 1, wherein the weight ratio of the composite resin:BMEP:HEMA:ethanol is 2:0.4-2.7:1:1.

3. The dental bonding agent of claim 1, further comprising an initiator, an accelerating agent, a stabilizing agent, or any combination thereof.

4. The dental bonding agent of claim 3, wherein the initiator is selected from a group consisting of benzoyl peroxide (BPO), acetyl peroxide, lauroyl peroxide (LP), and camphor quinone (CQ).

* * * * *